(12) United States Patent
Yarimizu et al.

(10) Patent No.: US 8,247,471 B2
(45) Date of Patent: Aug. 21, 2012

(54) POLYMERIZABLE COMPOSITION

(75) Inventors: Hideki Yarimizu, Itabashi-ku (JP); Hideki Tokui, Itabashi-ku (JP); Hiroto Minamisawa, Itabashi-ku (JP)

(73) Assignee: GC Corporation, Tokyo (JP)

( * ) Notice: Subject to any disclaimer, the term of this patent is extended or adjusted under 35 U.S.C. 154(b) by 191 days.

(21) Appl. No.: 12/725,657

(22) Filed: Mar. 17, 2010

(65) Prior Publication Data
US 2010/0240797 A1 Sep. 23, 2010

(30) Foreign Application Priority Data

Mar. 18, 2009 (JP) ................................ 2009-065415

(51) Int. Cl.
*C08F 20/10* (2006.01)
*C08F 4/76* (2006.01)
(52) U.S. Cl. ........................................ 523/118; 526/301
(58) Field of Classification Search .................. 526/301; 523/118
See application file for complete search history.

(56) References Cited

U.S. PATENT DOCUMENTS
4,343,921 A * 8/1982 Piestert .......................... 525/310
2010/0036075 A1 * 2/2010 Ishino et al. ................... 526/320

OTHER PUBLICATIONS
U.S. Appl. No. 12/835,216, filed Jul. 13, 2010, Yarimizu, et al.

* cited by examiner

*Primary Examiner* — Ling Choi
*Assistant Examiner* — Chun-Cheng Wang
(74) *Attorney, Agent, or Firm* — Oblon, Spivak, McClelland, Maier & Neustadt, L.L.P.

(57) ABSTRACT

To provide a dental adhesive composition which does not decrease preservation stability when reacting with acidity for acquiring dental adhesive property, even though using a filler having X-ray imaging property, and does not need the conventional mixing and kneading of two or more components, the dental adhesive composition includes (a) a (meth)acrylate compound having an acid group, and (b) aluminosilicate glass powder containing Sr and/or Ba and/or Ca, and the dental adhesive composition further includes a filler and (c) a photopolymerization catalyst, where the filler does not substantially make a neutralization reaction with the (meth)acrylate compound having an acid group as the (a) component because a filler content is 15% by weight or less in terms of oxide of $Al_2O_3$, and those coexist is one.

12 Claims, No Drawings

POLYMERIZABLE COMPOSITION

BACKGROUND OF THE INVENTION

1. Field of the Invention

The present invention relates to a polymerizable composition particularly used for a tooth treatment.

2. Description of the Conventional Art

The present invention relates to a polymerizable composition used by mixing one or more kinds of liquid and powder. More particularly, the present invention relates to such a polymerizable composition that a liquid composition does not gelate even though the liquid composition before polymerization is stored for a long period of time without being refrigerated, and a curing time does not change with time, that is, the curing time is neither delayed nor quickened by being stored.

A method of combining an organic peroxide and an aromatic tert-amine as a chemical polymerization catalyst has been conventionally used to cure a polymerizable composition at ordinary temperature, where the polymerizable composition includes a monomer, an oligomer, and a prepolymer of acrylate, methacrylate, or the like which have radical polymerization characteristic. In this method, curing time is controlled and preservation stability of the composition before polymerization is increased, by adjusting an amount of the organic peroxide blended with the liquid component and an amount of the aromatic tert-amine blended with the powder component, and also using a polymerization inhibitor together. However, the polymerizable composition has a problem that a cured body after polymerization is discolored while time passes by the aromatic tert-amine. In addition, the organic peroxide is unstable, so that the liquid component easily gelates before polymerization when a great amount of the organic peroxide is blended with a liquid component and the liquid component is stored for a long period. By contrast, when a great amount of the polymerization inhibitor is blended with the liquid component in order to secure long-term preservation stability, the curing time becomes very long. Therefore, the conventional polymerizable composition should be stored in a refrigerator for restraining the reaction of the organic peroxide.

As another chemical polymerization catalyst, a composition in combination of an organic aromatic compound including at least one —$SO_2$— group, a peroxide, and a aromatic tert-amine is used. However, since the organic peroxide and the aromatic tert-amine are used, there are still problems that a cured body discolors and preservation stability is low.

Further, a polymerization method of using trialkylborane is also known. However, trialkylborane has a disadvantage unable to be previously blended with the polymerizable composition including a (met)acrylate compound having radical polymerization characteristic since trialkylborane is oxidized easier than aromatic tert-amine. Therefore, trialkylborane should be stored in a vessel separately from the (meth) acrylate compound, and should be added to the polymerizable composition at each use. Thus, the operation is complicated.

The present inventors developed before a polymerizable composition including a ternary catalyst consisting of a pyrimidinetrione derivative, an organohalogen compound, and an organometallic compound, and applied a patent for this composition as in Japanese Patent Application Laid-Open No. 2003-105008. Since this composition does not include amine, a cured body does not discolor, and the composition can be used under acid conditions. However, the ternary catalyst still has a problem in preservation stability of the pyrimidinetrione derivative.

In addition to this, for example, Japanese Patent Application Laid-Open No. 58-219281 discloses a combination of cumene hydroperoxide and a thiourea derivative. This combination has higher thermal stability than that of conventional composition. However, a composition using the combination has a problem that a curing reaction of cumene hydroperoxide and a thiourea derivative is slow. Even if a blending concentration is sufficient, the composition cannot obtain a polymerization speed which is appropriate for dental adhesives.

In order to improve this composition, for example, Japanese Patent Application Laid-Open No. 2007-056020 discloses a combination of cumene hydroperoxide and acetylthiourea, for a redox reaction in the presence of a copper compound. Since this composition has comparatively high thermal stability and does not include an aromatic tert-aimine, a cured body does not discolor with time after cure. Further, this composition is not influenced by acid substituent of an acidic (meth)acrylate, where the acidic (meth)acrylate compound is conventionally blended in order to give adhesive property to a composition. Thus, the composition has excellent preservation stability. However, when an operator adheres a dental prosthesis to a tooth, a dental material is required particularly to have a property that the material is properly cured within a time desired by an operator, and to be constant in a curing time for every product. About these points, the combination still does not satisfy the requirements of stability of the curing time.

SUMMARY OF THE INVENTION

Problem to be Solved by the Invention

The present invention is directed to a polymerizable composition having more excellent preservation stability of a liquid component than that of a conventional composition using a combination of a copper compound, cumene hydroperoxide, and N-acetylthiourea, and having a curing time which does not change with time, that is, is neither delayed nor quickened from a time designed for the product even though the composition is stored.

Means for Solving the Problem

Present inventors carried out earnest works to solve the aforementioned problems, and as a result, they found out a polymerizable composition having excellent curability and excellent preservation stability by using a hydroperoxide as a peroxide, a thiourea derivative as a reducing material, and a vanadium compound as a polymerizarion accelerator, to complete the present invention.

The present invention is a polymerizable composition consisting of a liquid (including a paste) component which contains a (meth)acrylate compound and a hydroperoxide as a peroxide, and a powder component which contains a fluoroaluminosilicate glass, a thiourea derivative as a reducing material and a vanadium compound as a polymerization accelerator.

As for the polymerizable composition according to the present invention, if a part or whole of the (meth)acrylate compound is a(meth)acrylate compound having an acid group, the polymerizable composition can give adhesion effects to a tooth, and a ceramic such as zirconia and alumina and an alloy including noble metals which are used as dental restoratives.

Effect of the Invention

The polymerizable composition according to the present invention is an excellent polymerizable composition which has better preservation stability than that of a conventional composition using a combination of a copper compound, cumene hydroperoxide and N-acetylthiourea.

DETAILED DESCRIPTION OF PREFERRED EMBODIMENT

The (meth)acrylate compound in the present invention means various kinds of monomers, oligomers and prepolymers of acrylate or methacrylate. More particularly, the (meth)acrylate compound used in the present invention could be methyl(meth)acrylate, ethyl (meth)acrylate, isopropyl (meth)acrylate, n-butyl(meth) acrylate, isobutyl(meth) acrylate, hydroxypropyl(meth) acrylate, tetrahydrofurfryl(meth) acrylate, glycidyl (meth)acrylate, 2-hydroxyethyl(meth) acrylate, 2-hydroxypropyl(meth)acrylate, 3-hydroxypropyl (meth)acrylate, 2-methoxyethyl(meth)acrylate, 2-ethoxyethyl (meth)acrylate, 2-methoxyethyl(meth)acrylate, 2-ethylhexyl (meth) acrylate, benzyl(meth) acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1, 6-hexanediol di(meth) acrylate, trimethylolpropane tri(meth)acrylate, trimethylolethane tri(meth)acrylate, pentaerythritol tri(meth)acrylate, trimethylolmethane tri(meth)acrylate, pentaerythritol tetra (meth)acrylate, polybutylene glycol di(meth)acrylate, or bisphenol A diglycidyl(meth)acrylate. A monomer, oligomer, and prepolymer of these compounds can be properly used. Further, as for (meth)acrylates having urethane bond, there are di-2-(meth)acryloxyethyl-2,2,4-trimethylhexamethylene dicarbamate, 1,3,5-tris[1,3-bis{(meth)acryloyloxy}-2-propoxycarbonylaminohexane]-1,3,5-(1H, 3H, 5H) triazine-2,4,6-trione, and 2,2-bis-4-(3-(meth)acryloxy-2-hydroxypropyl)-phenylpropane, and the like. In addition, the (meth) acrylate having urethane bond includes (meth)acrylate of urethane oligomer consisting of 2,2'-di(4-hydroxycyclohexyl)propane, 2-oxypanone, hexamethylene diisocyanate, and 2-hydroxyethyl(meth)acrylate, (meth)acrylate of urethane oligomer consisting of 1,3-butanediol, hexamethylene diisocyanate, and 2-hydroxyethyl(meth)acrylate, and the like. These can be used independently or by mixing two or more kinds.

In the present invention, a (meth)actylate compound having an acid group can be used. It is one of characteristics that hydroperoxide is stable to both a (meth)acrylate compound not having an acid group and a (meth)acrylate compound having an acid group. The (meth)acrylate compound having an acid group has an effect for giving an adhesive property to the polymerizable composition to adhere to the tooth structure and dental restorative materials which are ceramics such as zirconia and alumina, and an alloy including noble metals. The (meth)acrylate compound having an acid group is preferably (meth)acrylate having a phosphate group or a carboxyl group. Thus, a (meth)acrylate compound having one or plural phosphate groups or carboxyl groups in one molecule can be used. Since the phosphate group has acidity stronger than the carboxyl group, the phosphate group has a high effect for dissolving a smear layer on a tooth surface and for tooth demineralization. Particularly, the phosphate group can exercise an effect for improving adhesive property to enamel. The (meth)acrylate compound having a phosphate group could be 2-(meth)acryloyloxyethyldihydrogen phosphate, bis[2-(meth)acryloyloxyethyl]hydrogen phosphate, 2-(meth)acryloyloxyethylphenylhydrogen phosphate, 6-(meth)acryloyloxyhexyldihydrogen phosphate, 6-(meth)acryloyloxyhexylphenylhydrogen phosphate, 10-(meth)acryloyloxydecyldihydrogen phosphate, 3-di(meth)acryloylpropane-2-dihydrogen phosphate, 1,3-di(meth)acryloylpropane-2-phenylhydrogen phosphate, bis[5-{2-(meth)acryloyloxyethoxycarbonyl}heptyl]hydrogen phosphate, or the like.

Particularly, 10-(meth)acryloyloxydecyldihydrogen phosphate is preferable because of having an excellent adhesive property and stability of the (meth)acrylate compound itself. These (meth)acrylate compounds having the phosphate group can be used independently or by mixing two or more kinds.

The (meth)acrylate compound having the carboxyl group could be 4-(meth)acryloxyethyltrimellitic acid, 4-(meth)acryloxyethyltrimellitic acid anhydride, 4-(meth)acryloxydecyltrimellitic acid, 4-(meth)acryloxydecyltrimellitic acid anhydride, 11-(meth)acryloyloxy-1,1-undecanedicarboxylic acid, 1,4-di(meth)acryloyloxypyromellitic acid, 2-(meth)acryloyloxyethylmaleic acid, 2-(meth)acryloyloxyethylphthalic acid, 2-(meth)acryloyloxyethylhexahydrophthalic acid, or the like. Particularly, 4-(meth)acryloxyethyltrimellitic acid and 4-(meth)acryloxyethyltrimellitic acid anhydride are preferable because of having an excellent adhesive property.

A polymerization reaction used for the polymerizable composition according to the present invention utilizes an oxidation-reduction reaction of a hydroperoxide and a thiourea derivative. In the liquid component, a hydroperoxide as a peroxide material is blended with a (meth)acrylate compound. In the powder component, a thiourea derivative as a reducing material and a vanadium compound as a polymerization accelerator are blended with a fluoroaluminosilicate glass.

The blending amount of the hydropexide in the liquid component is preferably 0.01 to 10% by weight. If the blending amount is less than 0.01% by weight, the function as a redox polymerization initiator tends to be insufficient. If the blending amount is more than 10% by weight, the polymerization becomes too rapid to be practical at the time of mixing the liquid component and the powder component. The hydroperoxide could be p-menthane hydroperoxide, diisopropylbenzene hydroperoxide, 1,1,3,3-tetramethylbutyl hydroperoxide, cumene hydroperoxide, tert-tetramethylbutyl hydroperoxide, or the like. Particularly, cumene hydroperoxide and tert-tetramethylbutyl hydroperoxide are preferable due to the reason of preservation stability.

The fluoroaluminosilicate powder is used as a primary component of the powder component for giving an X-ray imaging property to a kneaded material. The fluoroaluminosilicate glass powder includes $Al^{3+}$, $Si^{4+}$, $F^-$, and $O^{2-}$, as primary components, and preferably, further includes $Sr^{2+}$ and/or $Ca^{2+}$. In particular, as for preferable ratios of the primary components with respect to the total weight, $Al^{3+}$ is 10 to 21% by weight, $Si^{4+}$ is 9 to 21% by weight, $F^-$ is 1 to 20% by weight, and the total of $Sr^{2+}$ and $Ca^{2+}$ is 10 to 34% by weight. The fluoroaluminosilicate glass powder can be subjected to a surface treatment with a silane coupling agent, like a filler mentioned below.

The thiourea derivative is a reducing material for redox polymerization. The content of the thiourea derivative in the powder component is preferably 0.01 to 10% by weight. If the content is less than 0.01% by weight, the ability as a polymerization catalyst is insufficient. If the content is more than 10% by weight, a curing time is hard to stabilize. The thiourea derivative could be ethylenethiourea, diethylthiourea, tetramethylthiourea, N-acetylthiourea, N-benzoylthiourea, diphenylthiourea, dicyclohexylthiourea, or the like. Particularly, N-acetylthiourea and N-benzoylthiourea are preferable.

The vanadium compound is a polymerization accelerator for redox polymerization. The blending amount of the vanadium compound in the powder component is preferably 0.001 to 1% by weight. If the blending amount is less than 0.001% by weight, the effect as the polymerization accelerator tends to be insufficient. If the blending amount is more than 1% by weight, the polymerization becomes too rapid to be practical at the time of mixing the liquid component and the powder component. The vanadium compound could be vanadium acetylacetonate, vanadyl acetylacetonate, vanadyl stearate, vanadium naphthenate, vanadium benzoyl acetonate, or the like. Particularly, vanadium acetylacetonate and vanadyl acetylacetonate are preferable.

The polymerizable composition according to the present invention can include a filler component in the liquid component. Further, the polymerizable composition can include a filler other than fluoroaluminosilicate glass in the powder component. The filler component has an effect to increase the strength of the composition. The filler could be powder of anhydrous silicic acid, glasses such as barium glass, alumina glass, potassium glass, fluoroaluminosilicate glass, and the like, synthetic zeolite, calcium phosphate, feldspar, fumed silica, aluminum silicate, calcium silicate, magnesium carbonate, hydrous silicic acid, hydrous calcium silicate, hydrous aluminum silicate, quartz, or the like. In order to bond with (meth)acrylate compound, these fillers can be subjected to a surface treatment with a silane coupling agent such as γ-methacryloxypropyltrimethoxysilane, vinyltrichlorosilane, vinyltriethoxysilane, vinyltrimethoxysilane, vinyltriacetoxysilane, vinyltri (methoxyethoxy)silane, or the like. Further, a pre-polymerized filler produced by previously mixing the aforementioned filler with a monomer and/or an oligomer, curing the mixture, and pulverizing the cured product, can be used. These fillers are used independently or by mixing two or more. Particularly, anhydrous silicic acid, hydrous silicic acid, hydrous calcium silicate, and hydrous aluminum silicate have an effect for preventing the liquid component before polymerization from gelling even when being stored for a long period.

The mixing ratio of the liquid component and the powder component in the polymerizable composition according to the present invention is preferably 5:1 to 1:10 by weight. If the ratio is out of this range, the each of the polymerization catalysts hardly balances, so that some problems in the curing process could occur.

In addition, the polymerizable composition according to the present invention can properly include a photopolymerization catalyst, an antibacterial agent, a pigment, and the like, which are ordinarily used, if necessary. Further, in order to increase reactivity of (meth)acrylate compound having an acid group with respect to the tooth structure, the liquid component can include water.

EXAMPLES

Liquid components and powder components were produced with the blending ratios (% by weight) shown in Tables 2 to 4, and these were subjected to a test for preservation stability.

Abbreviations in the tables are as follows.

TEGDMA: Triethylene glycol dimethacrylate
UDMA: Di-2-methacryloxyethyl-2,2,4-trimethylhexamethylene dicarbamate
HEMA: 2-hydroxy methacrylate
MDP: 10-(meth)acryloyloxydecyldihydrogen phosphate
Aerosil: Fumed silica (the product name: R812, produced by Nippon Aerosil Corporation)
BPO: Benzoyl peroxide
DAC: Dimethyl ammonium chloride
BHT: Butylhydroxytoluene
p-amine: p-Tolyldiethanolamine
N-C5EPT: N-cyclohexyl 5 ethylpyrimidinetrione
AACu: Acetylacetone copper The blending ratios of the fluoroaluminosilicate glass powder are shown in Table 1.

TABLE 1

| | Fluoroaluminosilicate glass powders | | |
|---|---|---|---|
| | FG I | FG II | FG III |
| Aluminum oxide (g) | 21 | 23 | 22 |
| Anhydrous silicic acid (g) | 44 | 41 | 43 |
| Calcium fluoride (g) | 12 | 10 | 12 |
| Calcium phosphate (g) | 14 | 13 | 15 |
| Strontium carbonate (g) | 9 | 13 | 8 |

The fluoroaluminosilicate glass powder was produced by fully mixing raw materials, putting the mixture in a high temperature electric furnace at 120° C. for 5 hours so as to make a fused glass, cooling the fused glass quickly, pulverizing the glass for 10 hours with a ball mill, and passing the pulverized glass through a 200 meshe shieve (ASTM).

[Test for Confirming Preservation Stability]

In each of examples and comparative examples, the polymerizable composition was stored at a constant temperature of 23° C. and 50° C., and curing times were measured at a time of production and after 12 weeks. In a constant temperature room at 23±1° C., the liquid component of 1 g and the powder component of 2 g were weighed, taken on a kneading paper, and uniformly mixed for 15 seconds by a manual kneading operation with a spatula. An exothermic curve of the polymerizable composition was measured based on ISO4029: 2000 7.6. A reading method of the curing time was based on ISO4029:2000 7.8. These results were shown in Tables 5 to 7. In addition, although the compositions of examples and comparative examples were produced considering a product containing a photopolymerization catalyst (camphorquinone), the compositions were not irradiated with light in order to confirm preservation stability.

Clearly from Tables 2 to 7, it was confirmed that delay in curing of the polymerizable composition which includes an initiator consisting of a hydroperoxide, a thiourea derivative, and a vanadium compound is small, regardless of the different composition of (meth)acrylate compound conventionally used for a dental material, and regardless of the existence of (meth)acrylate compound having an acid group.

TABLE 2

|  |  |  | Example 1 | Example 2 | Example 3 | Example 4 | Example 5 |
|---|---|---|---|---|---|---|---|
| Liquid Component | Hydroperoxide | p-Menthane hydroperoxide | 1 | 1 |  |  |  |
|  |  | Cumene hydroperoxide |  |  | 1 | 1 |  |
|  |  | tert-Butylhydroperoxide |  |  |  |  | 2 |
|  | (Meth)acrylate | UDMA | 70 | 70 | 70 | 70 | 70 |
|  |  | TEGDMA | 20 | 20 | 20 | 20 | 20 |
|  |  | HEMA | 4 |  | 4 |  | 4 |
|  |  | MDP |  | 4 |  | 4 |  |
|  | Filler | Aerosil | 4.95 | 4.95 | 4.95 | 4.95 | 3.95 |
|  | Other | BHT | 0.05 | 0.05 | 0.05 | 0.05 | 0.05 |
| Powder Component | Thiourea Derivative | N-Acetylthiourea | 0.5 | 0.5 |  |  |  |
|  |  | N-Benzoylthiourea |  |  | 1 | 1 |  |
|  |  | Diphenylthiourea |  |  |  |  | 1 |
|  | Vanadium Compound | Vanadium acetylacetonate | 0.05 | 0.05 |  |  |  |
|  |  | Vanadyl acetylacetonate |  |  | 0.05 | 0.05 |  |
|  |  | Vanadyl stearate |  |  |  |  | 0.05 |
|  | Filler | FG I |  |  |  |  |  |
|  |  | FG II |  |  | 98.85 | 98.95 |  |
|  |  | FG III | 99.35 | 99.35 |  |  | 98.85 |
|  | Other | Camphorquinone | 0.1 | 0.1 | 0.1 | 0.1 | 0.1 |

TABLE 3

|  |  |  | Example 6 | Example 7 | Example 8 | Example 9 |
|---|---|---|---|---|---|---|
| Liquid Component | Hydroperoxide | p-Menthane hydroperoxide |  |  | 5 |  |
|  |  | Cumene hydroperoxide |  |  |  |  |
|  |  | tert-Butylhydroperoxide | 2 | 2 |  | 2 |
|  | (Meth)acrylate | UDMA | 70 | 67 | 70 | 70 |
|  |  | TEGDMA | 20 | 18 | 20 | 20 |
|  |  | HEMA |  |  |  |  |
|  |  | MDP | 4 | 4 | 4 | 4 |
|  | Filler | Aerosil | 3.95 | 3.95 | 4.95 | 3.95 |
|  | Other | BHT | 0.05 | 0.05 | 0.05 | 0.05 |
| Powder Component | Thiourea Derivative | N-Acetylthiourea |  | 0.5 |  |  |
|  |  | N-Benzoylthiourea |  |  | 10 |  |
|  |  | Diphenylthiourea | 1 |  |  | 1 |
|  | Vanadium Compound | Vanadium acetylacetonate |  | 0.05 |  |  |
|  |  | Vanadyl acetylacetonate |  |  | 0.05 |  |
|  |  | Vanadyl stearate | 0.05 |  |  | 0.5 |
|  | Filler | FG I | 98.85 |  |  | 98.4 |
|  |  | FG II |  |  |  |  |
|  |  | FG III |  | 99.35 | 89.85 |  |
|  | Other | Camphorquinone | 0.1 | 0.1 | 0.1 | 0.1 |

TABLE 4

|  |  |  | Comparative example 1 | Comparative example 2 | Comparative example 3 | Comparative example 4 | Comparative example 5 | Comparative example 6 |
|---|---|---|---|---|---|---|---|---|
| Liquid Component | Polymerization Catalyst | Cumene hydroperoxide |  |  |  |  | 1 | 1 |
|  |  | BPO | 1 | 1 |  |  |  |  |
|  |  | DAC |  |  | 0.5 |  |  | 0.5 |
|  | (Meth)acrylate | UDMA | 70 | 70 | 70 | 70 | 70 | 70 |
|  |  | TEGDMA | 19 | 19 | 19.5 | 20 | 20 | 19.5 |
|  |  | HEMA | 4 |  | 4 | 4 | 4 |  |
|  |  | MDP |  | 4 |  |  |  | 4 |
|  | Filler | Aerosil | 5.95 | 5.95 | 5.95 | 4.95 | 4.95 | 5.95 |
|  | Other | BHT | 0.05 | 0.05 | 0.05 | 0.05 | 0.05 | 0.05 |
| Powder Component | Polymerization Catalyst | N-Acetylthiourea |  |  |  |  | 1 | 1 |
|  |  | p-Amine | 1 | 1 |  |  |  |  |
|  |  | N-C5EPT |  |  | 1 |  |  | 1 |
|  |  | AACu |  |  | 0.05 |  | 0.05 | 0.05 |

TABLE 4-continued

|  |  | Comparative example 1 | Comparative example 2 | Comparative example 3 | Comparative example 4 | Comparative example 5 | Comparative example 6 |
|---|---|---|---|---|---|---|---|
| Filler | FG I |  |  | 98.85 | 98.9 | 98.85 | 98.85 |
|  | FG II |  | 98.9 |  |  |  |  |
|  | FG III | 98.9 |  |  |  |  |  |
| Other | Camphorquinone | 0.1 | 0.1 | 0.1 | 0.1 | 0.1 | 0.1 |

TABLE 5

|  |  |  | Example 1 | Example 2 | Example 3 | Example 4 | Example 5 |
|---|---|---|---|---|---|---|---|
| Preservation Stability [min.:sec.] | 23° C. | At the time of production | 5:00 | 6:00 | 4:00 | 4:30 | 4:30 |
|  |  | After 12 weeks | 6:00 | 7:00 | 4:15 | 4:45 | 4:45 |
|  | 50° C. | At the time of production | 5:00 | 6:00 | 4:00 | 4:30 | 4:30 |
|  |  | After 12 weeks | 6:15 | 7:15 | 4:15 | 4:45 | 5:00 |

TABLE 6

|  |  |  | Example 6 | Example 7 | Example 8 | Example 9 |
|---|---|---|---|---|---|---|
| Preservation Stability [min.:sec.] | 23° C. | At the time of production | 4:45 | 1:45 | 1:30 | 1:30 |
|  |  | After 12 weeks | 5:00 | 1:30 | 1:30 | 1:30 |
|  | 50° C. | At the time of production | 4:45 | 1:45 | 1:30 | 1:30 |
|  |  | After 12 weeks | 5:15 | 1:30 | 1:45 | 1:45 |

TABLE 7

|  |  |  | Comparative example 1 | Comparative example 2 | Comparative example 3 | Comparative example 4 | Comparative example 5 | Comparative example 6 |
|---|---|---|---|---|---|---|---|---|
| Preservation Stability [min.:sec.] | 23° C. | At the time of production | 4:30 | 8:00 | 5:00 | 8:00 | 6:00 | Not cured |
|  |  | After 12 weeks | Gelled (could not measure) | 13:00 | 7:00 | 13:00 | 8:00 | Not cured |
|  | 50° C. | At the time of production | 4:30 | 8:00 | 5:00 | 8:00 | 6:00 | Not cured |
|  |  | After 12 weeks | Gelled (could not measure) | Not cured | Not cured | Not cured | 9:30 | Not cured |

What is claimed is:

1. A polymerizable composition comprising:
   a liquid component comprising at least one (meth)acrylate compound and a hydroperoxide; and
   a powder component comprising:
      a fluoroaluminosilicate glass,
      a thiourea derivative, and
      a vanadium compound.

2. The polymerizable composition as claimed in claim 1, wherein the at least one (meth)acrylate compound is a (meth)acrylate compound having an acid group.

3. The polymerizable composition as claimed in claim 1 or 2, wherein the thiourea derivative is at least one selected from the group consisting of ethylenethiourea, diethylthiourea, tetramethylthiourea, N-acetylthiourea, N-benzoylthiourea, diphenylthiourea, and dicyclohexylthiourea.

4. The polymerizable composition as claimed in claim 1 or 2, wherein the vanadium compound is at least one selected from the group consisting of vanadium acetylacetonate, vanadyl acetylacetonate, vanadyl stearate, vanadium naphthenate, and vanadium benzoyl acetonate.

5. The polymerizable composition as claimed in claim 3, wherein the vanadium compound is at least one selected from the group consisting of vanadium acetylacetonate, vanadyl acetylacetonate, vanadyl stearate, vanadium naphthenate, and vanadium benzoyl acetonate.

6. The polymerizable composition as claimed in claim 1, wherein the hydroperoxide is at least one selected from the group consisting of p-menthane hydroperoxide, diisopropylbenzene hydroperoxide, 1,1,3,3-tetramethylbutyl hydroperoxide, cumene hydroperoxide and tert-tetramethylbutyl hydroperoxide.

7. The polymerizable composition as claimed in claim 1, wherein a content of the hydroperoxide in the liquid component is from 0.01 to 10% by weight.

8. The polymerizable composition as claimed in claim 1, wherein a content of the thiourea derivative in the powder component is from 0.01 to 10% by weight.

9. The polymerizable composition as claimed in claim 1, wherein the liquid component further comprises a filler.

10. The polymerizable composition as claimed in claim 1, wherein the powder component further comprises a filler which is selected from the group consisting of anhydrous silicic acid, barium glass, alumina glass, potassium glass, fluoroaluminosilicate glass, synthetic zeolite, calcium phosphate, feldspar, fumed silica, aluminum silicate, calcium silicate, magnesium carbonate, hydrous silicic acid, hydrous calcium silicate, hydrous aluminum silicate and quartz.

11. The polymerizable composition as claimed in claim 1, wherein the liquid component does not comprise water.

12. The polymerizable composition as claimed in claim 2, wherein the (meth)acrylate compound having an acid group is a (meth)acrylate compound having a phosphate group which is selected from the group consisting of 2-(meth)-acryloyloxyethyldihydrogen phosphate, bis[2-(meth)acryloyloxyethyl]hydrogen phosphate, 2-(meth)acryloyloxyethylphenylhydrogen phosphate, 6-(meth)acryloyloxyhexyldihydrogen phosphate, 6-(meth)acryloyloxyhexylphenylhydrogen phosphate, 10-(meth)acryloyloxydecyldihydrogen phosphate, 1, 3-di(meth)acryloylpropane-2-dihydrogen phosphate, 1, 3-di(meth)acryloylpropane-2-phenylhydrogen phosphate and bis[5-{2-(meth)acryloyloxyethoxycarbonyl} heptyl] hydrogen phosphate.

* * * * *